United States Patent [19]
Sleeter

[11] 4,102,646
[45] Jul. 25, 1978

[54] QUANTITATIVE ANALYSIS OF CARBOHYDRATES BY INFRARED SPECTROSCOPY

[76] Inventor: Ronald T. Sleeter, 1263 Semor Dr., Decatur, Ill. 62521

[21] Appl. No.: 785,163

[22] Filed: Apr. 6, 1977

[51] Int. Cl.² .......................................... G01N 21/30
[52] U.S. Cl. ................................ 23/230 R; 250/338; 250/339; 356/51
[58] Field of Search ...................... 23/230 R; 356/51; 250/338, 339

[56] References Cited

U.S. PATENT DOCUMENTS

| | | | |
|---|---|---|---|
| 3,539,804 | 11/1970 | Billetdeaux | 250/339 |
| 3,694,158 | 9/1972 | Lauer | 23/230 R |
| 3,698,866 | 10/1972 | Grassetti | 23/230 R |

OTHER PUBLICATIONS

D. A. Skoog et al., "Fundamentals of Analytical Chem.", 661–669, Holt, Rinehart & Winston, New York, 1963.
E. R. Garrett et al., J. Pharm. Sci., 58(10), Oct. 1969, 1224–1227.
J. W. White et al., Anal. Chem., 30(4), Apr. 1958, 506–510.
L. M. J. Verstraeten, Anal. Chem., 36(6), May 1964, 1040–1044.
Sugar Industry Abstracts, 22:88 (1960), I.
Sugar Industry Abstracts, 27:703 (1965), II.
Sugar Industry Abstracts, 29:208 (1967), III.

*Primary Examiner*—Sidney Marantz
*Attorney, Agent, or Firm*—Plumley and Tyner

[57] ABSTRACT

A qualitative and quantitative method for analyzing a chemical composition for its carbohydrate content. An infrared spectrum of the composition produced in selected wave length ranges is compared with those produced from standard samples. Applications include analysis of fructose and dextrose in corn syrups and determination of Dextrose Equivalent (D.E.) of corn syrups.

6 Claims, 1 Drawing Figure

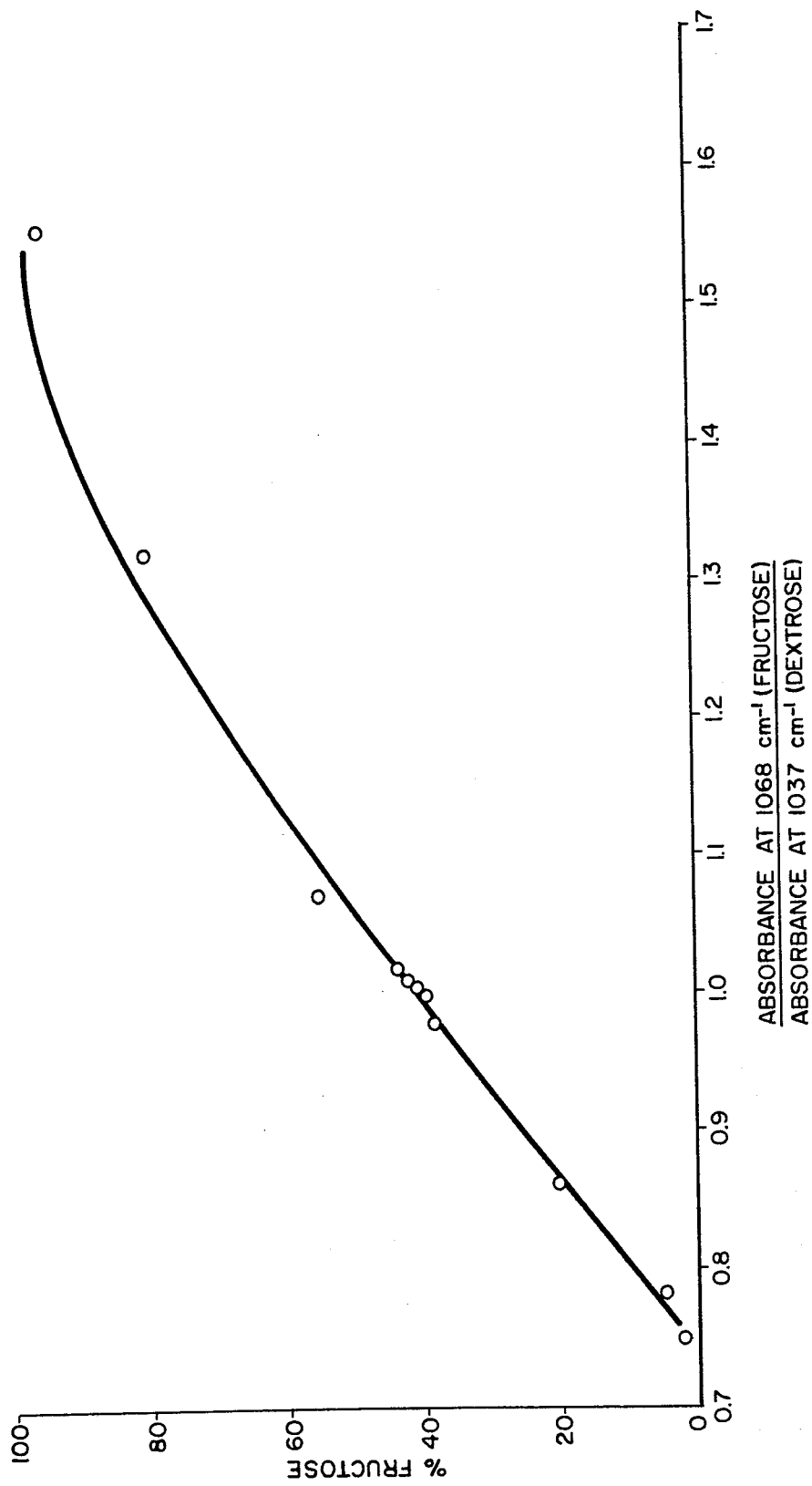

QUANTITATIVE ANALYSIS OF CARBOHYDRATES BY INFRARED SPECTROSCOPY

BACKGROUND OF THE INVENTION

This invention relates to a method of rapid and precise analysis, both quantitatively and qualitatively, for carbohydrates, and in particular, this invention relates to a method for regular syrups, fructose syrups, and blends of syrups or carbohydrates with sucrose to determine constitutional makeup.

There have been four main procedures in the past for the quantitative analysis of fructose and dextrose in syrups or for the analysis of other syrup and starch compositions.

(1) The method of polarimetry is described in U.S. Pat. No. 3,694,158 and is believed to be the first feasible system for the continuous analysis of a process stream to detect the amounts of dextrose and fructose in mixtures simultaneously. This procedure has the disadvantage, however, of producing imprecise results if the composition contains appreciable amounts (over two percent) of higher homologs of dextrose, i.e. degree of polymerization of 2–10 or higher, e.g. maltooligosaccharides. Furthermore, the method becomes inaccurate if the tested composition contains mixtures of three or more types of sugars. The method is also sensitive to variations in temperature, thus requiring a controlled atmosphere.

(2) High pressure liquid chromatography has been developed to where it is capable of analyzing carbohydrate solutions containing fructose, dextrose, higher homologs of these sugars, and still other sugars. The method is capable of providing an automatic analysis in a period of time of 10–30 minutes. A discussion of this procedure may be found in AACC Paper No. 48, Oct. 5–8, 1976, Annual Meeting In New Orleans, La. by H. D. Scobell. Other than the inordinate length of time to obtain the analysis results, this process appears to be a suitable technique except where there are blends containing sucrose or maltose, or where there are appreciable quantities of maltulose, etc. These components elute simultaneously with other constituents of the analyzed sample and yield imprecise results.

(3) Gas/liquid chromatography is an earlier procedure than high pressure liquid chromatography and it is capable of quantitative analysis of a carbohydrate composition to determine the various sugars present in one analytical scan. The difficulty with this procedure is that it requires a precise technique in the preparation of samples and in the derivatization of samples. Furthermore, the analytical time, not including the sample preparation time, is inordinantly long, i.e. about 20 minutes. See K. M. Brobst and C. E. Lott, Am. Soc. Brew. Chem. Proc. 71–75 (1966).

(4) There are many chemical procedures for the quantitative analysis of dextrose, fructose, higher sugars, and mixtures of sugars. Illustrative of such analytical techniques are:

(a) Cystein carbazole method for the determination of ketose sugars, Corn Refiners Tentative Method E-1, Jan. 6, 1976;

(b) "The Quantitative Determination of Glucose, Fructose, and Sucrose in Fruits and Potatoes", E. S. Della Monica et al, J. Food Sci. 39, pp. 1062-3 (1974);

(c) "Spectrophotometric Analyses Of Glucose And Mixture Of Glucose, Fructose, And Sucrose", E. Garrett and J. Young, J. Pharm, Sci. 58, pp. 1224-7 (1969); and (d) "Dextrose Equivalent", Corn Refiners Method E-26. These are all wet chemical analyses which have substantially the same disadvantages of the possibility of technician error, the requirement of large amounts of bench space and analytical equipment, and the large amount of time involved in the analysis. Furthermore, these techniques are either so specific that they are capable of analyzing only a single type of sugar or they are so non-specific that they are incapable of distinguishing one type of sugar from another.

The present invention provides an analytical process which overcomes these disadvantages. It is extremely fast in that it can provide a complete analysis in 1–3 minutes, frequently less than 1 minute. There is no necessity for derivatization nor is there a need to carefully control the amount of solids in the sample. It is preferable to have anomeric equilibrium in the mixtures analyzed. This technique is capable of analyzing samples containing from less than 1 percent up to 100 percent solids and it is capable of installation on a production line for continuous or semi-continuous analysis of process streams. The technique is capable of handling higher sugars as well as mixtures of sugars. It is capable of providing information as to carbohydrate complex formations, such as fructose-$H_3BO_3$. It is also capable of providing an analysis of the degree of anomerization and the rate of anomerization. The process is also able to provide information as to the extent of derivatization and other behavorial questions such as carbohydrate anomerization in acids, bases, and organic solvents.

The present invention is based on infrared (IR) analysis of carbohydrates. While IR spectra of carbohydrates have been studied and characterized for many years [two reviews have been published: "Infrared Spectra of Carbohydrates" by W. Brock Neely, in ADVANCES IN CARBOHYDRATE CHEMISTRY, 12 13–33 (1957) and "Infrared Spectroscopy and Carbohydrate Chemistry" by H. Spedding in ADVANCES IN CARBOHYDRATE CHEMISTRY, 19 23–49 (1964)] it was not immediately apparent that IR could be used as a qualitative/quantitative analytical tool. This position was taken in a paper by W. J. Hoover, et al. in J. FOOD SCIENCE, 30 253–261 (1965) "Isolation and Evaluation of the Saccharide Components to Starch Hydrolysates II. Evaluation" where it was stated with reference to hydrolyzed starch, "No trends were noted in shifts of peaks or development of peaks with increase in molecular weight (from dextrose) . . . The spectra of all of the saccharides were so similar that they could not be used in identifying or distinguishing between the various malto-oligosaccharides." Furthermore, a paper "Infrared Spectra of Carbohydrates in Water and a New Measure of Mutarotation" by Frank S. Parker in BIOCHIM. BIOPHYS. Acta. 42 513–519 (1960) indicates that the absorbance at 1143 $cm^{-1}$ is the most indicative band for observing mutarotation of $\alpha$- and $\beta$-glucose. In accordance with the present invention absorbances at 1038 $cm^{-1}$ and 1080 $cm^{-1}$ provide much more useful information.

Very little infrared work has been done specifically for fructose. Typical of that work is that which is described in "Identification of the Anhydrides of D-Fructose from the 'Fingerprint' Region of their Infrared Spectra" by W. W. Binkley, et. al., INTERNATIONAL SUGAR JOURNAL 73 259–261 (1971), which clearly is not directed at the analytical purposes of the present invention.

SUMMARY OF THE INVENTION

The present invention provides a process for qualitatively and quantitatively analyzing a chemical composition for its content of starch or sugars comprising:

(1) Subjecting a sample of a chemical composition to infrared spectroscopy to produce a spectrum;

(2) Noting the amplitude of the absorbances at the known frequencies for each species or family of species (wherein "family of species" means, for example, dextrose, maltose and higher homologs, e.g. maltooligosaccharides) of carbohydrate; and (3) comparing each noted amplitude with known amplitudes for standard samples of that same specie or family of species to determine the amount of that specie or family of species in the composition.

Two basic types of infrared instruments and associated techniques are utilized for this work. One infrared analytical technique employed in this process is infrared Fourier transform spectroscopy which has been known as an instrumental technique for the past few years after the first commercial instruments were developed in the late 1960's. The preferred type of instrument utilizes a Michelson Interferometer which produces an interferogram of the sample being analyzed. The interferogram is then subjected to a calculation by a digital computer in accordance with a mathematical procedure known as "Fourier transform" to yield the frequency spectrum. It is an alternative procedure to employ the Hadamard transform to produce the frequency spectrum. This type of spectroscopy has already found wide and diversified applications in areas such as a quality control technique for determining impurities in semi-conductors, and it is also an excellent detector for use in connection with the various chromatography analyses. Other applications for this type of spectroscopy are the remote monitoring of hot gas emission from smoke stacks wherein the technique involves a telescope to observe the emissions from a remote location, the identification of microscopic particles, the detection of minor additives in a composition, and routine spectroscopy performed by conventional grating spectrophotometers.

This type of spectroscopy is applicable over a very wide spectral range from about 10,000 $cm^{-1}$ in the near infrared frequencies to 10 $cm^{-1}$ in the far infrared frequencies. This method is capable of providing precise finger printing of organic molecules exhibiting fine absorbances in the mid range of 4,000 $cm^{-1}$ to 400 $cm^{-1}$. Resolution may be obtained over the entire spectral range to a value better than 0.1 $cm^{-1}$.

Conventional infrared dispersive spectrophotometers using prisms or gratings and filters to scan the various wavelengths of interest may also be used as the second basic type of spectrophotometer. Modern microprocessor and computer controlled infrared spectrophotometers utilizing scale expansion can scan from 4000 $cm^{-1}$ to 32 $cm^{-1}$ with better than 0.2 $cm^{-1}$ resolutions. These instruments are capable of scanning spectra to produce the resolution required for this analysis in 8 minutes. Furthermore since the analysis for the present invention requires scanning from about 1800 $cm^{-1}$ to 700 $cm^{-1}$, preferably 1200 $cm^{-1}$ to 800 $cm^{-1}$, or the region of 700 $cm^{-1}$ to 50 $cm^{-1}$, the analysis may be performed in less than 2 minutes. With the computer and microprocessor controlled instruments the spectrum need not be scanned, since the instrument can report the amplitudes of absorbances at discrete wavelengths. The time for such an analysis is much less than 1 minute, and a computer makes the necessary computations needed to complete the analysis.

The present invention provides a method of rapid quantitative and qualitative analysis of starch, starch derivatives, and all of the specific sugars, examples of which are dextrose, fructose, lactose, galactose, and sucrose whether separate or mixed with each other. This method yields information as to the composition of regular corn syrup, the Dextrose Equivalent (DE), amount of dextrose, etc. The analysis may be performed on water solutions of the compounds, glassy amorphous solids or pelletized solids. Further types of information which can be obtained include the solids content, anomeric conformation, complex formation with other compounds, reaction and anomerization rate studies, degree of derivatization, behavior of carbohydrates in solutions of acids, bases, salts, or organic solvents, and othe/similar information.

The process involves the analysis of standard samples containing known amounts of known compounds to determine the absorbances and frequencies of such samples to serve as standard samples against future analyses of unknown compositions. The standard samples are normally correlated into a graph for purposes of interpolation. The unknown sample is analyzed by infrared spectroscopy and the amplitude of the absorbance and the frequency are compared with measurements on standard samples to determine the amount of a particular carbohydrate which is present in the composition.

The preferred apparatus and procedures used for analyses in accordance with this invention are as follows:

(1) Cell Windows — Irtran 2 windows of ZnS and $BaF_2$ windows for the Fourier transform spectroscopy and conventional infrared spectroscopy. Cell windows may be of other materials, such as ZnSe.

(2) Cell Thickness — 12.5, 15, or 25 microns (3) Number Of Scans — 250, 125, 30, and 1

(4) Resolution — 4 wave members (5) Word No. — 32 bit words (6) Instrument — Digilab IRFTS 15 equipped with a double beam head; Perkin Elmer 283 with 580 infrared Spectrophotometer; or Nicolet 7199 FT-FR System (7) Light — monochromatic, e.g. by employing filters, lasers, etc.

(8) Concentration — 10–30% solids preferred, wider ranges if desired (9) Sample Preparation — Anomeric equilibrium attained prior to analysis of sample. Equilibrium obtained either by allowing solution to reach equilibrium by natural action or by the addition of several drops of ammonium hydroxide when speed is necessary.

(10) Analysis Of Unknowns — Samples of fructose corn syrup and regular corn syrup analyzed by high pressure liquid chromatography for carbohydrate composition and by CRA Method E-26 for DE in regular corn syrups.

In order to more fully understand the present invention the following examples of the operation of this invention serve to illustrate the scope and nature of the invention. Parts and percentages are by anhydrous weight unless otherwise noted.

EXAMPLE 1

Mixtures of fructose and dextrose ranging from 2% fructose/98% dextrose to 98% fructose/2% dextrose prepared such that when distilled water was added a 30% solids solution was obtained. Several drops of ammonia solution were added to each sample to ensure anomerization to equilibrium. After a complete solution was obtained, each sample was placed in a cell made from Irtran II windows with a cell thickness of approximately 12.5 microns. An infra-red Fourier transform spectroscopic analysis was run on each sample using as the primary parameters 250 scans, 4 wave number resolutions and 32 bit words. The instrument employed was Digilab IRFTS 15 with a double beam head. The ratios of the absorbances of fructose at 1068 cm$^{-1}$ and of dextrose at 1037 cm$^{-1}$ were computed and plotted against the known values for the proportion of fructose to dextrose in each sample. The result was a nearly linear plot as shown in FIG. 1 in the attached drawing.

Unknown samples were then analyzed by the same process, the ratios of absorbances were computed and the proportion of fructose to dextrose determined from this plot. When this proportion was checked by other known procedures, such as chromatography the results were found to be accurate.

EXAMPLE 2

In the same manner described in Example 1 tests were performed on other sugars, such as lactose, galactose, maltose, maltotriose, and sucrose, and even including starch. In each instance, the analytical technique was found to be accurate and the analytical time varied from less than one minute to not more than 3 minutes.

EXAMPLE 3

In the same manner described in Example 1 analyses were made on known samples and mixtures of samples of alpha-D-glucose and beta-D-glucose to determine the applicability of this technique for the study of anomerization rates. Thirty scans were run by IRFTS, thus allowing an analysis time of 27 seconds. Analyses were made at time intervals so as to obtain a value for the reaction rate.

EXAMPLE 4

Employing the same procedures as in Example 1 an experiment was run to determine the applicability of the technique for establishing the Dextrose Equivalent (DE). Pure compounds of dextrose, maltose, maltotriose, and starch were tested by this spectroscopic technique to establish their frequencies and absorbances. Syrups having a known DE were also tested in the same fashion. By computing ratios of the amplitude of absorbances against values of DE a linear plot was obtained. Unknown syrups were then subjected to the same analytical technique and the ratios of the amplitude of absorbances were computed and applied to the plot. The technique is applicable not only to mixtures of two sugars but also to mixtures containing at least five sugars. Data from the plot yielded a good correlation of IR-computed DE with actual DE of the unknown syrups determined by chemical analyses.

EXAMPLE 5

The analyses described in Examples 1-4 inclusive were performed on a Perkin Elmer 283 and 580 Infrared Spectrophotometer. The resolution was 3.7 cm. The scan time from 1500 cm$^{-1}$ to 900 cm$^{-1}$ was about 2 minutes. Solutions of 30% solids were employed and 2 drops of ammonium hydroxide were added to produce complete anomerization. The analytical results were substantially identical to those produced in Examples 1-4.

Although the invention has been described in considerable detail with reference to certain preferred embodiments thereof, it will be understood that variations and modifications can be effected within the spirit and scope of the invention as described hereinabove and as defined in the appended claims.

What is claimed is:

1. A proccess for qualitatively and quantitatively analyzing a chemical composition for its content of starch or sugars which comprises:
    (a) subjecting a sample of said composition to infrared spectroscopy at wave lengths in the region of 1800-700 cm$^{-1}$ or the region of 700-50 cm$^{-1}$ to produce a spectrum;
    (b) noting the amplitude of the absorbances at the known frequencies for each carbohydrate or family of carbohydrates, and
    (c) comparing each noted amplitude with known amplitudes for standard samples of that same carbohydrate or family of carbohydrates to determine the amount of that carbohydrate or family of carbohydrates present in the composition.

2. The process of claim 1 wherein the carbohydrates or family of carbohydrates are selected from the group consisting of lactose, galactose, fructose, dextrose, maltose, maltotriose, maltooligosaccharides, sucrose, alpha-D-glucose, beta-D-glucose, starch, and modified starches.

3. The process of claim 1 wherein a fructose corn syrup is analyzed for its proportionate amounts of dextrose and fructose at frequencies of 1037 cm$^{-1}$ and 1068 cm$^{-1}$.

4. The process of claim 1 wherein the spectroscopy is Fourier transform spectroscopy.

5. The process of claim 1 wherein the spectroscopy is dispersive infrared spectroscopy.

6. The process of claim 1 wherein the spectroscopy is performed at discrete wave lengths using monochromatic light.